United States Patent [19]
Young et al.

[11] Patent Number: 5,763,593
[45] Date of Patent: Jun. 9, 1998

[54] NUCLEIC ACIDS ENCODING TBP-ASSOCIATED GLOBAL NEGATIVE REGULATOR

[75] Inventors: Richard A. Young, Weston; Ellen L. Gadbois; David M. Chao, both of Cambridge, all of Mass.

[73] Assignee: Whitehead Institute for Biomedical Research

[21] Appl. No.: 681,812

[22] Filed: Jul. 29, 1996

[51] Int. Cl.$^6$ .......................... C07H 21/02; C07H 21/04
[52] U.S. Cl. .......................................................... 536/23.74
[58] Field of Search .................................. 536/23.1, 23.7, 536/23.24; 435/6, 69.1, 71.1, 91.1, 172.1, 172.3, 254.2, 254.21; 530/350

[56] References Cited

FOREIGN PATENT DOCUMENTS

94/17087  8/1994  WIPO .

OTHER PUBLICATIONS

Collart et al. Genes & Development 8: 525–537, 1994.
Peterson et al. Cell 64: 1135–1143, Mar. 1991.
Roeder et al. Mol. Cell. Biol. 5: 1543–1553, Jul. 1985.
Xie, X., et al., "Structural Similarity Between TAFs and the Heterotetrameric Core of the Histone Octamer," *Nature*, 380:316–322 (1996).
Hoffmann, A., et al., "A Histone Octamer–Like Structure Within TFIID," *Nature*, 380, 356–359 (1996).
Goodrich, J.A., et al., "Contacts in Context: Promoter Specificity and Macromolecular Interactions in Transcription," *Cell*, 84:825–830 (1996).
Inostronza, J., et al., Dr1, a TATA–Binding Protein–Associated Phosphoprotein and Inhibitor of Class II Gene Transcription, *Cell*, 70:477–489 (1992).
Meisterernst, M., et al., "Activation of Class II Gene Transcription by Regulatory Factors is Potentiated by a Novel Activity," *Cell* 66: 981–993 (1991).
Meisterernst, M., et al., "Family of Proteins That Interact with TFIID and Regulate Promoter Activity," *Cell*, 67:557–567 (1991).
Wilson, C.J., et al., "RNA Polymerase II Holoenzyme Contains SWI/SNF REgulators Involved in Chromatin Remodeling," *Cell*, 84:235–244 (1996).
Struhl, K., "Chromatin Structure and RNA Polymerase II Connection: Implications for Transcription," *Cell*, 84:179–182 (1996).
Merino, et al., "DNA Topoisomerase I Is Involved in Both Repression and Activation of Transcription," *Nature*, 365:227–232 (1993).
Wolffe, A.P., "Transcription: In Tune with the Histone," *Cell*, 77:13–16 (1994).
Koleske, A.J. and Young, R.A., "The RNA Polymerase II Holoenzyme and its Implications for Gene Regulation," *Trends Biochem. Sci.*, 20:113–116 (1995).
Koleske, A.J. and Young, R.A., "An RNA Polymerase II Holoenzyme Responsive to Activators," *Nature*, 368:466–467 (1994).

Thompson, C.M., et al., "A Multisubunit Complex Associated with RNA Polymerase II CTD and TATA–Binding Protein in Yeast," *Cell*, 73:1361–1375 (1993).
Kingston, R.E., et al., "Repression and Activation by Multiprotein Complexes That Alter Chromatin Structure," *Genes & Dev.*, 10:905–920 (1996).
Rothstein, R., "Targeting, Disruption, Replacement, and Allele Rescue: Integrative DNA Transformation in Yeast," *Methods in Enz.*, 194:281–301 (1991).
Boeki, J.D., et al., "5–Fluoroorotic Acid as a Selective Agent in Yeast Molecular Genetics," *Methods in Enzymology*, 154:164–175 (1987).
Hengartner, C.J., et al., "Association of an Activator with an RNA Polymerase II Holoenzyme," *Genes & Dev.*, 9:897–910 (1995).
White, R.J., et al., "Differential Regulation of RNA Polymerases I, II, and III by the TBP–Binding Repressor Dr1," *Science*, 266:448–450 (1994).
Arents, G., et al., "The Nucleosomal Core Histone Octamer at 3.1 Å Resolution: A Tripartite Protein Assembly and a Left–Handed Superhelix," *Proc. Natl. Acad. Sci. USA*, 88:10148–10152 (1991).
Baxevanis, A.D., et al., "A Variety of DNA–Binding and Multimeric Proteins Contain the Histone Fold Motif," *Nucleic Acids Research*, 23(14):2685–2691 (1995).
Elledge, S.J and David, R.W., "A Family of Versatile Centromeric Vectors Designed for use in the Sectoring–Shuffle Mutagenesis Assay in *Saccharomyces cerevisiae*," *Gene*, 70:303–312 (1988).
Goppelt, A., et al., "A Mechanism for Repression of Class II Gene Transcription Through Specific Binding of NC2 to TBP–Promoter Complexes via Heterodimeric Histon Fold Domains," *EMBO J.*, 15(12):3105–3116 (1996).
Halle, J–P. and Miesterernst, M., "Gene Expression: Increasing Evidence for a Transcriptosome," *Trends In Genet.*, 12(5):161–163 (1996).
Roeder, R.G., "The Role of General Initiation Factors in Transcription by RNA Polymerase II," *Trends Biochem. Sci.*, 21:327–335 (1996).
Kaiser, K. and Meisterernst, M., "The Human General Co–Factors," *Trends Biochem. Sci.*, 21:342–345 (1996).
Kim, J., et al., "A Negative Cofactor Containing Dr1/p19 Modulates Transcription With TFIIA in a Promoter–Specific Fashion," *J. Biol. Chem.*, 271(31):18405–18412 (1996).
Yeung, K.C., et al., "Structure–Function Analysis of the TBP–Binding Protein Dr$_1$ reveals a Mechanism for Repression of Class II Gene Transcription," *Genes & Dev.*, 8:2097–2109 (1994).

(List continued on next page.)

*Primary Examiner*—George C. Elliott
*Assistant Examiner*—Thomas G. Larson
*Attorney, Agent, or Firm*—Hamilton, Brook, Smith and Reynolds, P.C.

[57] ABSTRACT

A eukaryotic, global negative regulator of class II transcription, DNA sequences encoding the negative regulator and results demonstrating the activity of the purified negative regulator protein to repress class II transcription are described.

7 Claims, 3 Drawing Sheets

OTHER PUBLICATIONS

Kim, T.K., et al., "TATA–Binding Protein Residues Implicated in a Funcational Interplay Between Negative Cofactor NC2 (Dr1) and General Factors TFIIA and TFIIB," *J. Biol. Chem.*, 270(18):10976–10981 (1995).

Koleske, A., et al., "Purification of Yeast RNA Polymerase II Holoenzymes," *Methods in Enzymology*, 273:176–184 (1996).

Kretzschmar, M., et al., "Identification of Human DNA Topoisomerase I as a Cofactor for Activator–Dependent Transcription by RNA Polymerase II," *Proc. Natl. Acad. Sci. USA*, 90:11508–11512 (1993).

Mermelstein, F., et al., "Requirement of a Corepressor for Dr1–Mediated Repression of Transcription," *Genes & Dev.*, 10:1033–1048 (1996).

Thompson, C.G. and Young, R.A., "General Rerquirement for RNA Polymerase II Holoenzymes in vivo," *Proc. Natl. Acad. Sci. USA*, 92:4587–4590 (1995).

International application No.: PCT/US97/13364, International Search Report, mailed from the Patent Corporation Treaty 29 Nov. 1997.

Kim, S.J., et al., "The Dr1/DRAP1 Heterodrimer is a Global Repressor of Transcription In Vivo," *Proc. Natl. Acad. Sci. USA*, 94:820–825 (1997).

Gadbois, E.L., et al., "Functional Antagonism Between RNA Polymerase II Holoenzyme and Global Negative Regulator NC2 In Vivo," *Proc. Natl. Acad. Sci. USA*, 94:3145–3150 (1997).

Goppelt, A. and Meisterernst, M., "Characterization of the Basal Inhibitor of Class II Transcription NC2 from *Saccharomyces Cerevisiae*," *Nucleic Acids Res.*, 24(22):4450–4455 (1996).

Kraus, V.B., et al., "Interaction of the Dr1 Inhibitory Factor With the TATA Binding Protein is disrupted by Adenovirus E1A," *Proc. Natl. Acad. Sci. USA*, 91:6279–6282 (1994).

FIG. 1B

NCB1 gene sequence (yNC2α/DRAP1 protein)

```
-108 ttttattttgggcattaaaacgaaaaaaagcacgtcacgaaataaaattcaaaaaataaaaaaaccagttacagtactcatcactacattctta 1 atggcagatcaagtaccagttacaacacacaactgaggtaccacttgatgctggagggagtccagtagtaacatggtgtaccaactcg
     M  A  D  Q  V  P  V  T  T  Q  L  P  P  I  K  P  E  H  E  V  P  L  D  A  G  G  S  P  V  G  N  M  G  T  N  S 109 aataacaacgagctagtgatgtattcgacagatgtgtttgaccagataaagaaacacactttccctccggccaagttaaagaaaataatgcagacagagaccgaggatataggaaaagtttca
     N  N  N  E  L  G  D  V  F  D  R  I  K  T  H  F  P  P  A  K  V  K  K  I  M  Q  T  D  E  D  I  G  K  V  S 217 caagccacgccccgtaatagcgggcaggtcctagagttttttatagcgttattggtgaaaaaagcggggagatggcaagagacaaggaaccaagagaataaccgcc
     Q  A  T  P  V  I  A  G  R  S  L  E  F  F  I  A  L  L  V  K  K  S  G  E  M  A  R  G  Q  G  T  K  R  I  T  A 325 gaaatactaaaaaaacaattttaaacgacgaaaaattcgatttcttaagggaaggtctatgcgtagaagaaggcgtcgaggaaccgcaaccgaggagagagagagtgcctgagca
     E  I  L  K  K  T  I  L  N  D  E  K  F  D  F  L  R  E  G  L  C  V  E  E  G  Q  T  Q  P  E  E  E  S  A  *

433 gaacggggcgatgtaacttagtgtaaatgaataccacatctatatatatcatataccaatgtattttatatctatatatgtctgcacatatatatattatactctatta
```

FIG. 1C yeast vs human NC2α/DRAP1

```
yeast  42  LGDVFDRIKTHFPPAKVKKIMQTDEDIGKYSQATPVIAGRSLEFFIALLVKKSGEMARGQGTKRITAEILKKTILNDEKFDFLREGL.CVEEGQTQPEEE   140
           :::||::|||:|||||||||||||||::|||:|||||||||||||:::|:::|:|||||:|:|||||||||||||||||||||||::|:|:||:||||:||||
human   1  MPSKKKKYNARFPPARIKKIMQTDEEIGKVAAVPVIISRALELFLESLLKKACQVTQSRNAKTMTTSHLKQCIELEQQFDFLKDLVASVPDMQGGEDN     100
                                         ─────────     ─────────────                 ────────────
                                          helix 1                  helix 2                      helix 3
```

FIG. 1D

NCB2 gene sequence (yNC2 β/Dr1 protein)

```
-108 tcgccctgctcgccttgtcgattctatcgtgcagagttaccagtataaggtgggcaagaaatcataacgatatttactaatacagttgtacctattaattaattg 1 atggctggagactcgatataatgtgtcgcttccaaggtgtatgttagttatattgttgcaaaactcaagctttgatgcgggtactgagcggttatactaacttaga
     M  A  G  D  S  D  N  V  S  L  P  K  A 109 gaaacactgaatgatcttagcgaccgtacaaaagatgatatctgaaatactggaccaggattttgatgttttaccaaggatgcaagagaaatcatcatcaactccggca
     T  V  Q  K  M  I  S  E  I  L  D  Q  D  L  M  F  T  K  D  A  R  E  I  I  N  S  G  I 217 tagaattcatataatgatcctgtcctgatggcttccgaaatggccgacaagaggctaagaaaaccatagcccgacacgtgatcaaagctagaagagttggagt
     E  F  I  M  I  L  S  S  M  A  S  E  M  A  D  N  E  A  K  K  T  I  A  P  E  H  V  I  K  A  L  E  E  L  E  Y 325 ataatgagtttataccattcttagagagaaatattattgaattttaaggttcccagaagattccaagttcaagaagtcaggtctctgaag
     N  E  F  I  P  F  L  E  E  I  L  L  N  F  K  G  S  Q  K  V  K  E  T  R  D  S  K  F  K  K  S  G  L  S  E  E 433 aaggagctacgacaacaagagagttgtttagacagtcaaggtccagattacaccacagtatctgatccgttaagtggaggattcttcttgaatagaag
     E  L  L  R  Q  E  E  L  F  R  Q  S  R  L  H  H  N  S  V  S  D  P  V  K  S  E  D  S  S  *

541 ctttctaaacaaagtaatgctatatacgaaataaccacatggaatatgttaagcatgtaataaaaacgaagacaagtccaaaaaaaagaacg
```

FIG. 1E yeast vs human NC2 β/Dr1

```
yeast   2  AGDSDNVSLPKATVQKMISEILDQDLMFTKDAREIINSGIEFIMILSSMASEMADNEAKKTIAPEHVIKALEELEYNEFIPFLEEILLNFKGSQKVKET   101
           .| .:.:|:|.|||||  .:|||||||||  |:||: ||||:|:||||||||| ::|||||:.| .|||||||:|||||.|||||::.|  :|| |.:
human   5  SGNDDLTIPRAAINKMIKETL.PNVRVANDARELVVNCCTEFIHLISSEANEICNKSEKKTISPEHVIQALESLGFGSYISEVKEVLQECKTVALKRRK   103
           ———————————————————— ————————————————————————————————————————————————————————————————————————
                   helix 1                           helix 2                               helix 3 yeast 102  RDSKFKKSGLSEEELLRQQEELF..........RQSRSRLHHNSVSDPVKSEDSS    146
           |:|  |:| |:|||||||:|||:          |:|:   :|.::
human 104  ASSRLENLGIPEEELLRQQQELFAKARQQQAELAQQEWLQMQQAAQQAQLAAASAS  159
```

NUCLEIC ACIDS ENCODING TBP-ASSOCIATED GLOBAL NEGATIVE REGULATOR

BACKGROUND OF THE INVENTION

The regulation of cellular gene expression occurs primarily at the level of transcription initiation by RNA polymerase. Regulated transcription initiation by RNA polymerase II in higher eukaryotes involves the formation of a complex with general transcription factors at promoters (Sawadogo, M. and Sentenac, A., *Ann. Rev. Biochem.* 59:711–754 (1990). One of these factors, transcription factor IID (TFIID), contains the TATA-binding protein (TBP), which is able to bind directly to promoter DNA. The remaining components of the transcription initiation complex include RNA polymerase II and the initiation factors TFIIA, TFIIB, TFIIE, TFIIF, TFIIH, and TFIIJ. These components associate with TFIID-bound promoter DNA to form a transcription initiation complex. Sequence-specific DNA-binding proteins appear to regulate the establishment and activity of transcription initiation complexes, possibly through interactions with TFIIB and TBP and additional factors that make up TFIID.

Recently it has been shown that eukaryotic class II gene expression involves the recruitment of TBP multisubunit complexes and RNA polymerase II holoenzymes to promoters. (Goodrich, J. A. Cutler, G. & Tjian, R. *Cell* 84, 825–30 (1996); Halle, J. P. & Meisterernst, M. *Trends Genet* 12, 161–3 (1996); Koleske, A. L. & Young, R. A. *Trends Biochem Sci* 20, 113–6 (1995); Struhl, K. *Cell* 84, 179–82 (1996)). Negative cofactors have been purified from human cells that can associate with TBP or TFIID and inhibit transcription in vitro. (Goppelt, A., et al., *EMBO J.*, 15:3105–3116 (1996); Inostroza, J. A., Mermelstein, F. H., Ha, I., Lane, W. S. & Reinberg, D. *Cell* 70, 477–89 (1992); Kretzschmar, M., Meisterernst, M. & Roeder, R. G. *Proc Natl Acad Sci USA* 90, 11508–12 (1993); Merino, A., Madden, K. R., Lane, W. S., Champoux, J. J. & Reinberg, D. *Nature* 365, 227–232 (1993); Meisterernst, M. & Roeder, R. G. *Cell* 67(55), 7–67 (1991); Meisterernst, M., Roy, A. L., Lieu, H. M. & Roeder, R. G. *Cell* 66, 981–93 (1991)) but it is not known whether they function generally at promoters in vivo.

SUMMARY OF THE INVENTION

The present invention relates to the identification of a eukaryotic, global negative regulator of class II transcription. As described herein, a yeast global negative regulator protein complex, referred to herein as NC2 (DRAP1/Dr1), has been identified, cloned and sequenced. NC2 (DRAP1/Dr1) protein has been purified and its biological activity to suppress class II transcription has been demonstrated. The yeast NC2 (DRAP1/Dr1) global negative regulator protein is also referred to herein as yNC2.

More specifically, yeast NC2 (DRAP1/Dr1) binds to TATA-binding protein (referred to herein as TBP) and suppresses (e.g., partially inhibits or completely inhibits) transcription mediated by the RNA polymerase II holoenzyme in vitro. As discussed herein, global defects in mRNA synthesis caused by the SRB4-defective holoenzyme (Thompson, C. M. & Young, R. A. *Proc Natl Acad Sci USA* 92, 4587–90 (1995)) are alleviated by the yeast NC2 (DRAP1/Dr1) suppressing mutation in vivo. These results support the function of yeast NC2 (DRAP1/Dr1) as a global negative regulator of eukaryotic class II transcription that antagonizes RNA polymerase II holoenzyme function.

In one embodiment of the present invention, the yeast NC2 (DRAP1/Dr1) negative regulator protein, which comprises two protein subunits, NC2α/DRAP1 and NC2β/Dr1 (SEQ ID NOS:2, 4 and 5), is described. Specifically encompassed by this invention is the yeast NC2 (DRAP1/Dr1) protein complex, the amino acids encoding the protein complex comprising two NC2(DRAP1/Dr1) protein subunits, NC2α (SEQ ID NO.: 2) and NC2β (SEQ ID NOS: 4 and 5) and variants or derivatives (e.g., mutant yeast NC2(DRAP1/Dr1) proteins) thereof, and antibodies reactive with the yNC2 protein, either the protein complex, the two protein subunits thereof, or partial components of the protein complex or protein subunits.

Encompassed by this invention are the nucleic acid sequences (DNA or RNA) encoding the yeast NC2 (DRAP1/Dr1) negative regulator protein complex (SEQ ID NOS: 1 and 3), the nucleic acid sequence encoding the (SEQ ID NO.: 1) subunit also referred to herein as NCB and the nucleic acid sequence encoding the β subunit (SEQ ID NO.: 3), also referred to as NC2β2. Also encompassed are the complementary strands of these nucleic acid sequences, nucleic acid sequences that selectively hybridize to the yNC2 sequences under conditions described herein, and allelic variations thereof. Also encompassed by the present invention are nucleic acid probes comprising all, or a portion of SEQ ID NOS: 1 and 3, that are sufficiently complementary to a yNC2 nucleic acid sequence that they selectively hybridize to the yNC2 nucleic acid sequences.

This invention further relates to methods of modifying class II gene transcription by substances (e.g., antibodies or drugs) that bind to, or interact with the yNC2 negative regulator protein; the genes encoding the yNC2 protein, or the yNC2 mRNAs. Such substances can interact with the yNC2 negative regulator resulting in the modification (either increase or decrease) of RNA polymerase II holoenzyme mediated transcription. For example, a substance that binds to yNC2 can inhibit the binding of yNC2 to TBP, or yNC2 interaction with other transcription factors essential to gene transcription repression or inhibition. Moreover, differences in NC2 protein homologs (e.g., differences in the yeast and human NC2 (DRAP1/Dr1) negative regulator gene or protein sequences) can be exploited to design therapeutic compounds or drugs, that target pathogenic eukaryotes, e.g., the fungus Candida, and inhibit gene transcription in the pathogen without affecting gene transcription in the human host.

Another embodiment of the present invention relates to screening methods to identify substances, both naturally-occurring, and synthetic, that modify gene transcription. Specifically encompassed are screening methods comprising in vitro transcription mediated by the RNA polymerase II holoenzyme and the use of these methods to identify substances that interact with yNC2 and thus modify gene transcription.

Yet another embodiment of this invention further relates to methods of detecting yNC2 or homologous eukaryotic NC2 genes and gene products in a cell, or in biological fluids using nucleic acid probes which hybridize to DNA encoding the yNC2 protein, or to yNC2 mRNA, (e.g., antisense nucleotides) or antibodies which bind to the yNC2 gene product.

As described herein, results demonstrate that yeast NC2 (DRAP1/Dr1) is a conserved, essential, and global negative regulator of class II transcription that functions by antagonizing RNA polymerase II holoenzyme activity. Also as described herein, results demonstrate that relief from NC2 (DRAP1/Dr1) inhibition is a required step during transcription initiation at most class II promoters in vivo. These results provide new insights into the relationships between the positive and negative factors in transcription initiation at class II promoters in vivo.

BRIEF DESCRIPTION OF THE DRAWINGS

FIG. 1a. FIG. 1a is a schematic of a model showing the interaction of various components of RNA polymerase II holoenzyme mediated transcription.

FIG. 1b. FIG. 1b depicts the DNA sequence NCB1, encoding the yNC2α/DRAP1 protein (SEQ ID NO: 1; open reading frame (ORF) YER159c on chromosome V, Gen-Bank accession number U18917).

FIG. 1c. FIG. 1c shows the yeast (SEQ ID NO:2) and human (SEQ ID NO: 6) NC2α/DRAP1 protein alignment. Vertical lines indicate identity; colons, comparison value >0.5; and dots, comparison value >0.1 as defined by the program BESTFIT. Underlined regions indicate sequence, homologous to the α-helices in the histone fold structure of histone H2A.

FIG. 1d. FIG. 1d shows the DNA sequence NCB2, encoding the yNC2β/Dr1 protein (SEQ ID NO:3) (open reading frame (ORF) D9509.16 on chromosome IV, Genbank accession number U32274) with a predicted intron.

FIG. 1e. FIG. 1e shows the yeast (SEQ ID NO:4 and 5) and human (SEQ ID NO: 7) NC2β/Dr1 protein alignment. Underlined regions indicate sequence homologous to the α-helices in the histone fold structure of histone H2B.

DETAILED DESCRIPTION OF THE INVENTION

Figure 1A:
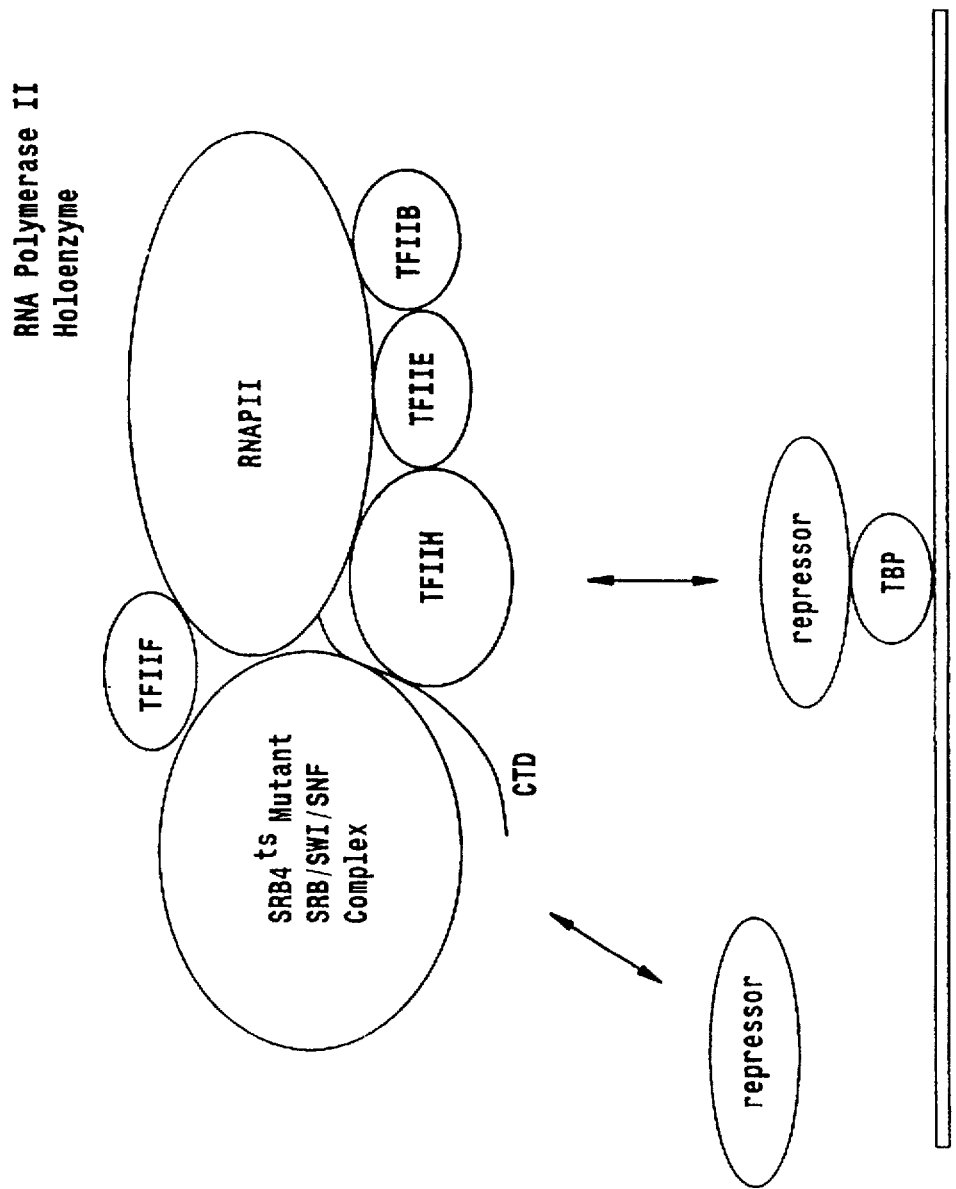

For the first time, a global negative regulator associated with the RNA polymerase II holoenzyme which mediates eukaryotic class II transcription has been described in yeast. Specifically, yeast NC2 (DRAP1/Dr1), or yNC2, has been identified as a global negative regulator of eukaryotic transcription mediated by the RNA polymerase II holoenzyme.

The identification of yeast NC2 resulted from work described herein based on the premise that if negative regulatory factors exist that repress global transcription initiation by RNA polymerase II holoenzyme in living cells, then defects in these negative regulators should compensate for defects in the holoenzyme. Genetic selection revealed that a defect in a yeast homologue of the human TBP-binding negative regulator NC2 (DRAP1/Dr1) suppresses a mutant (Thompson, C. M. & Young, R. A. *Proc Natl Acad Sci USA* 92, 4587–90 (1995) yeast RNA polymerase II holoenzyme function.

The RNA polymerase II holoenzyme components, SRB proteins, are essential for transcription at the majority of class II genes in *S. cerevisiae*. Because some SRB proteins play a positive role in holoenzyme function, it was reasoned that a defect in a specific positive SRB protein, SRB4, might be alleviated by defects in general negative regulators. To identify mutations that compensate for a defect in SRB4, spontaneous extragenic suppressors of the conditional srb4-138 allele were isolated as described in Example 1. One of the recessive suppressing genes was cloned, and the gene sequence (SEQ ID NO: 1) predicts a 142-amino acid protein with a molecular mass of 15,500 (15.5 K) (SEQ ID NO:2).

A search of sequence databases revealed that the predicted protein has 39% identity over 99 amino acids to the NC2α/DRAP1 subunit of human NC2 (DRAP/Dr1) (SEQ ID NO: 6; FIG. 1c). The gene encoding the putative yeast NC2α/DRAP1 protein was named NCB1. Deletion analysis revealed that NCB1 is essential for cell viability. The mutation present in the suppressing allele, ncb1-1, produces a 27 residue C-terminal truncation in the yeast NC2α/DRAP1 protein (FIG. 1b). Since NCB1 is an essential gene, the truncation mutation must cause a partial functional defect in the NC2α/DRAP1 protein.

Human NC2 (DRAP1/Dr1) consists of two subunits, NC2α/DPAP1 and NC2α/Dr1, both of which are necessary for maximal binding to TBP and repression of transcription in vitro. To determine if there is a yeast homologue of the NC2α/Dr1 subunit, the yeast database was searched with the human NC2β/Dr1 amino acid sequence. An open reading frame was identified (SEQ ID NO: 3) that predicts a 146 amino acid protein with a molecular mass of 16,700 (16.7 K) (SEQ ID NOS: 4 and 5) which is 37% identical to human NC2β/Dr1 (SEQ ID NO: 7) (FIG. 1d and e). A DNA clone that contains the coding sequence for the putative yeast NC2β/Dr1 homologue was isolated and its sequence confirmed. This gene was named NCβ2.

The human NC2 (DRAP1/Dr1) subunits each contain sequence predicting a histone fold structure. (Goppelt, A., et al., *EMBO J.* 15:3105–3116 (1996); Mermelstein, F., et al., *Dev* 10, 1033–48 (1996); Arents, G., Burlingame, R. W., Wang, B. C., Love, W. E. & Moudrianakis, E. N. *Proc Natl Acad Sci USA* 88, 10148–52 (1991); Baxevanis, A. D., Arents, G., Moudrianaki; E. N. & Landsman, D. *Nucleic Acids Res* 23, 2685–2691 (1995)). The yeast NC2 (DRAP1/Dr1) subunits also contain this sequence similarity (FIG. 1c and e). Interestingly, the C-terminal truncation in the ncb1-1 suppressing allele removes part of the histone fold in the yeast NC2α/DRAP1 subunit. Deletions in the human NC2 (DRAP1/Dr1) histone folds have been shown to decrease subunit association, TBP binding, and transcriptional repression. (Goppett, A., et al., *EMBO J.* 15:3105–3116 (1996); Mermelstein, F., et al., *Dev* 10, 1033–48 (1996)).

If the two yeast gene products are genuine homologs of human NC2 (DRAP1/Dr1), they would be expected to co-purify and bind to TBP. To determine whether this is the case, a yeast whole cell extract was subjected to GST and GST-TBP affinity chromatography as described in Example 2. Western analyses of the column eluates confirmed that both yeast NC2α/DRAP1 and NC2β/Dr1 proteins were specifically retained on the GST-TBP column. The eluate from the GST-TBP column was further purified over two ion-exchange columns Silver staining and Western analyses showed that yeast NC2α/DRAP1 and NC2β/Dr1 coeluted over both columns, and that the proteins appear to be in equal stoichiometry. These data confirm that the proteins encoded by NCB1 and NCB2 are stoichiometric subunits of a complex which can bind specifically to TBP.

The ability of a defective form of yeast NC2 (DRAP1/Dr1) to suppress the mutant RNA polymerase II holoenzyme suggests that yeast NC2 (DRAP1/Dr1) normally functions to repress holoenzyme activity. The ability of purified yeast NC2 (DRAP1/Dr1) to repress transcription mediated by the RNA polymerase II holoenzyme in vitro was tested as described in Example 3. A preparation of yeast NC2 (DRAP1/Dr1) from a strain containing an epitope-tagged NC2α/DRAP1 subunit gave material of higher yield and purity than from the TBP-affinity column. In vitro transcription reactions were performed with holoenzyme and fractions from the final column of this yeast NC2 (DRAP1/Dr1) purification. Repression of transcription correlated with the peak of yeast NC2 (DRAP1/Dr1) protein, demonstrating the biochemical activity predicted by the genetic suppression.

The observation that loss of NC2 (DRAP1/Dr1) function in yeast cells can compensate for a defect in the SRB4 component of the holoenzyme, together with previous evidence that SRB4 functions globally as a class II promoters (Thompson, C. M. & Young, R. A. *Proc Natl Acad Sci USA* 92, 4587–90 (1995), suggests that NC2 (DRAP1/Dr1) may repress transcription at class II promoters in general. To determine whether yeast NC2 (DRAP1/Dr1) functions at the majority of class II promoters in vivo, it was investigated whether the shutdown of mRNA synthesis observed in cells with the SRB4 temperature sensitive mutant srb4-138 is reversed by the loss of NC2 (DRAP1/Dr1) function as described in detail in Example 4. The results showed that upon shifting cells to the restrictive temperature, the growth rate of the srb 4-138 strain was severely reduced, whereas the srb4-138 ncb1-1 suppressor strain was only modestly affected. The levels of poly(A)+mRNA in these cells were measured immediately before and at several times after the shift to the restrictive temperature. There was a significant decrease in the mRNA population in the srb4-138 strain, as observed previously in Thompson, C. M. & Young, R. A. *Proc Natl Acad Sci USA* 92, 4587–90 (1995). In contrast, there was only a modest decrease in mRNA levels in the srb4-138 ncb1-1 strain after the temperature shift. Thus, the ncb1-1 mutation suppresses the general defect in transcription of class II messages caused by the srb4-138 mutation.

S1 analysis of individual class II transcripts confirmed that the decline in specific mRNAs in the srb4-138 strain reversed in the srb4-138 ncb1-1 strain. These results indicate that yeast NC2 (DRAP1/Dr1) has a general negative effect on the transcription of class II messages in vivo, and that a partial loss of NC2 (DRAP1/Dr1) repression compensates for the RNA polymerase II holoenzyme defect in the srb4-138 mutant strain.

The results described herein demonstrate that yeast NC2 (DRAP1/Dr1) is a conserved, essential, and global negative regulator of class II transcription that functions by antagonizing RNA polymerase II holoenzyme activity. The only other proteins known to have these properties are the histones (Kingston, R. E., Bunker, C. A. & Imbalzano A. N. *Genes Dev* 10, 905–920 (1996); Wolffe, A. P. *Cell* 77, 13–6 (1994), which share structural features with NC2 (DRAP1/Dr1). These results demonstrate that relief from NC2 (DRAP1/Dr1) inhibition is a required step during transcription initiation at most class II promoters in vivo. These data suggest a model of pre-initiation complex formation in which the holoenzyme, and possibly other factors, must surmount multiple layers of negative regulation in order to initiate transcription.

The present invention encompasses the yNC2(DRAP1/Dr1) protein complex comprising two subunits, yNC2α and yNC2β, their amino acid sequences, (SEQ ID NOS: 2, 4 and 5, respectively) and functional or biologically active variants, homologs or derivatives thereof. A "functional or biologically active protein" is defined herein as a protein which shares sufficient identity with the corresponding sequences of the described protein and possesses one or more of the biological functions thereof. Specific functions of the yNC2 protein include activities that modify class II transcription mediated by the RNA polymerase II holoenzyme, for example, repressing transcription by binding to TBP and blocking transcription initiation by the holoenzyme or interacting with histones or other proteins containing histone fold motifs. Biological function also includes the antigenicity of the protein defined herein as characteristics of the yNC2 protein that are immunogenic, i.e., characteristics of the protein have the ability to elicit the production of antibodies, or an antibody response.

Specifically intended to be encompassed by the present invention are the yNC2 amino acid sequences, as well as sequences analogous to, or homologous with, the yNC2 proteins, which include one, or more "silent changes" in the amino acid sequence. Such silent changes in the amino acid sequence may not reflect the exact yNC2 amino acid sequences described herein, but nevertheless, do not alter the essential biological function, or activity of the yNC2 protein, i.e., as a global negative regulator of eukaryotic transcription mediated by the RNA polymerase II holoenzyme. For example, one, or more, amino acid residue(s) may differ in an amino acid sequence (e.g., a few residues may be deleted or added) from the yNC2 amino acid sequence described herein, yet still retain the biological ability to function as a negative regulator of gene transcription. Alternatively, the protein may be truncated e.g., at one terminus, yet still retain biological function. Such proteins are referred to herein as biologically active fragments, or functional equivalents, of the yNC2 negative regulator protein. These functional equivalents of the yNC2 negative regulator can be identified by screening for biological activity to repress class II transcription mediated by the RNA polymerase II holoenzyme as described herein.

Also encompassed by the present invention are analogous proteins, or homologs of the yNC2 proteins that have either increased or decreased biological activity relative to wild-type, or naturally-occurring yNC2 proteins.

Also encompassed by this invention are the isolated and/or recombinant nucleic acid sequences (DNA and RNA) encoding the yNC2 protein, the complementary strands of these nucleic acid sequences, and nucleic acid sequences that are substantially complementary to a yNC2 DNA/RNA sequence to selectively hybridize to the yNC2 DNA/RNA sequence, e.g., SEQ ID NOS: 1 and 3.

Nucleic acids referred to herein as "isolated" are nucleic acids which have been separated away from the nucleic acids of the genomic or cellular nucleic acids of their source of origin (e.g., as the nucleic acid exists in cells or in a library) and may have undergone further processing. Isolated nucleic acids are obtained by methods known to those of skill in the art and by the methods described herein. These isolated nucleic acids include essentially pure nucleic acids, nucleic acids produced by chemical synthesis, by combinations of biological and chemical methods and recombinant nucleic acids that are isolated.

Substantially complementary is defined herein to mean that the nucleic acid sequence may not reflect the exact sequence described herein, e.g., SEQ ID NOS: 1 or 3, but must be sufficiently similar in identity to hybridize with SEQ ID NOS: 1 or 3, or a portion thereof, under appropriate stringency conditions, i.e., conditions sufficient for selective hybridization of the nucleic acids. For example, non-complementary bases can be interspersed in the sequence, or the sequence can be longer or shorter, provided that the sequence has sufficient complementary bases to selectively hybridize with SEQ ID NOS:1 or 3.

Conditions of stringency sufficient to identify nucleic acid sequences with substantial nucleic acid sequence identity are known to those of skill in the art. It is reasonable to believe that e.g., DNA sequences identified under such stringent conditions will likely encode a protein (also referred to herein as a polypeptide, or peptide fragment) with a biological activity comparable to yNC2 as described above. A general description of stringent hybridization conditions are discussed in Ausebel, F. M., et al., *Current Protocols in Molecular Biology*, Greene Publishing Assoc. and Wiley-Interscience, 1989, the teachings of which are incorporated herein by reference. Factors such as sequence length, base composition, percent mismatch between the hybridizing sequences, temperature and ionic strength influence the stability of nucleic acid hybrids. Thus, stringency conditions sufficient to identify additional yNC2 proteins (e.g., high or moderate stringency conditions) can be determined empirically, depending, in part, on the characteristics of the known DNA to which other unknown nucleic acids are being compared for sequence similarity.

Another embodiment of this invention relates to methods of modifying gene transcription by substances that bind to, or interact with, the yNC2 protein, or either of the individual subunits, yNC2α and yNC2β, or the DNA/RNA encoding yNC2 or the subunit proteins and, thus, modify the influence of yNC2 on RNA polymerase II mediated gene transcription. Thus, gene transcription can be up-regulated (i.e., stimulated) or down-regulated (i.e., repressed) via the yNC2 protein.

Specifically encompassed are methods that stimulate transcription mediated by the RNA polymerase II holoenzyme by inhibiting an appropriate level of the repressive activity of yNC2. For example, as described above, yNC2 binds to TBP. This binding antagonizes, or represses holoenzyme activity and results in the repression of transcription. An effective amount of a substance that binds to, or interacts with yNC2 or the DNA/RNA encoding yNC2, can partially or essentially completely, inhibit this repressive activity, thus, stimulate gene transcription mediated by the RNA polymerase II holoenzyme.

As defined herein, an amount of a substance sufficient to stimulate transcriptional activity is an amount sufficient to detectably increase transcription mediated by the RNA polymerase II holoenzyme without affecting cell viability. For example, effective amounts of a mutant yNC2 protein can be introduced into the cell. The mutant protein is incapable of repressing RNA polymerase II holoenzyme mediated transcription, yet competes with wild-type yNC2 for TBP binding, resulting in stimulating gene transcription.

Transcription of DNA sequences, or translation of mRNA sequences, encoding the yNC2 protein can be inhibited or decreased, resulting in decreased production of, or complete absence of yNC2 protein. Gene transcription can be modified by introducing an effective amount of a substance into a cell that inhibits transcription of the yNC2 gene, or that inhibits translation of mRNA encoding the yNC2 gene products. For example, antisense oligonucleotide sequences can be introduced into the cell that will hybridize with the gene encoding the yNC2 protein and inhibit transcription of the gene. Alternatively, an antisense sequence can be introduced into the cell that will interfere with translation of the mRNA encoding the yNC2 protein.

Alternatively, repression of RNA polymerase II holoenzyme mediated transcription can be achieved by increasing the amount of yNC2 present in a cell. For example, a vector containing a DNA insert encoding yNC2 can be introduced into the cell using techniques well known to those of skill in the art. Genetically altered, or mutant yNC2 can be used wherein the mutant yNC2 has a greater affinity for TBP, resulting in e.g., increased TBP-binding and repression of RNA polymerase II holoenzyme mediated transcription.

Repression of RNA polymerase II holoenzyme mediated transcription can also be achieved for example, with an antibody specific for yNC2 which would exert a stabilizing effect on the yNC2/TBP complex.

Substances used in the methods described herein can be nucleic acids or substances that are proteinaceous in nature, such as peptides (comprised of natural and non-natural amino acids) and peptide analogs (comprised of peptide and non-peptide components), or can be non-proteinaceous in nature, such as small organic molecules. The substance can also be a genetically engineered yeast negative regulator protein with an altered amino acid sequence. These substances would be designed to bind to, or interact with the yNC2 protein based on the DNA or amino acid sequences of the yNC2 protein described herein, or the antibodies reactive with the yNC2 protein described herein. Monoclonal or polyclonal antibodies specific for the intact yNC2 or either of the yNC2α or yNC2β subunits, or fragments thereof, can be used.

The substances described in the present invention can be identified and tested for their ability to modify gene transcription using an in vitro transcription assay. For example, DNA of interest (i.e., DNA to be transcribed) can be admixed with purified RNA polymerase II, the SRB and/or SWI/SNF proteins, transcription factors b, e, g or a (or homologies thereof), TBP, histones, or proteins with histone fold motifs, and other necessary transcriptional components along with the substance to be tested to produce a combination of reagents, or a test mixture. This test mixture is maintained under the appropriate conditions, i.e., conditions sufficient for DNA transcription to occur. DNA transcription can be assessed by determining the quantity of mRNA produced. DNA transcription is determined in the presence of the substance being tested and compared to DNA transcription in the absence of the test substance taking place under identical conditions (e.g., a control mixture). If DNA transcription occurs to a lesser extent in the test mixture (i.e., in the presence of the substance being evaluated) than in the control mixture, the substance has interacted with yNC2 in such a manner as to repress, or down-regulate, DNA transcription. If DNA transcription occurs to a greater extent in the test mixture than in the control mixture, the substance has interacted with yNC2 in such a manner as to stimulate, or up-regulate, DNA transcription.

The yNC2 protein can also be genetically altered, such as by site directed mutagenesis, resulting in a yNC2 protein with altered activity. Genetically altered yNC2 protein would affect gene transcription. For example, genetically altered yNC2 protein may be introduced into a cell via a liposome, or linked to a carrier protein known to cross the cell membrane. Alternatively, DNA encoding such a protein may be introduced into the cell using, for example, a vector containing the DNA sequence via standard laboratory procedures. These genetically altered yNC2 proteins would be impaired in their ability to interact with e.g., TBP, thus stimulating . RNA polymerase II holoenzyme mediated transcription. In addition, DNA encoding a wild-type yNC2 protein with biological activity (e.g., being capable of participating in gene transcription) may be introduced into the cell to supplement a diminished supply of endogenous yNC2 protein. The wild-type yNC2 protein would be expressed in the cell, thus increasing the level of yNC2, resulting in repression of RNA polymerase II mediated gene transcription.

As described herein, yNC2 has been demonstrated as being essential for cell viability. Therefor it is also reasonable to believe that inhibition of yNC2 activity above a threshold level can detrimentally affect cells because of the partial loss of repressive activity. It is reasonable to believe that, for example, if the yNC2 repressive activity is substantially inhibited, uncontrolled transcription resulting in uncontrolled cellular activity would occur, eventually leading to cell death. Thus, an effective amount of a substance can sufficiently inhibit yNC2 activity such that cell death results. An effective amount of a substance which results in cell death can be determined using the methods described herein.

The ability to modify gene transcription is useful in three categories of human disease: 1) inherited, or genetic, disease; 2) acquired disease, not of infectious origin; and 3) acquired disease, of infectious origin. Changes in gene transcription in these three situations will contribute to changes in the manifestation of the disease.

For example, in an inherited disease, the level of expression of a critical gene is altered relative to the expression of the gene in an individual who does not manifest the disease. If the amount of gene product produced is inadequate, the introduction of a substance into a cell which interacts with yNC2 protein, resulting, for example, the in stimulation of gene transcription, increased gene product will result, thus, improving the condition of the individual.

In the example of an acquired disease that is not of infectious origin, such as cancer, modifying gene transcription will also modify the disease state. Typically a cancer is the result of the loss of growth control concomitant with increased transcriptional activity, in a particular cell type. In this case, increasing yNC2 activity in a cancer cell, thus repressing gene transcription and cell growth, will improve the condition of the individual. Because cancer cells have an extraordinarily high rate of gene transcription, the substances will significantly affect the rate of gene transcription in cancer cells, (i.e., rapidly growing cells) but insignificantly affect the rate of gene transcription in normal cells (analogous to the use of anti-metabolites in the treatment of cancer).

In the case of acquired disease where the disease is the result of an infectious agent, such as a bacterium or a virus, an increase in the transcription of genes encoding proteins involved in the immune response would result in the improvement of the condition of the individual. For example, in HIV infection, a substance which interacts with yNC2 protein could be targeted for delivery to lymphocytic cells, resulting in the increase of transcription of important lymphocytic proteins. Also, in the case of some virus infections, such as vaccinia virus, host cell gene transcription is completely shut down by the virus. A substance as described above, targeted to the virally infected cells, would turn on the host cell's transcription machinery. Alternatively, for some viruses, e.g., adenovirus, it may be advantageous to turn down the host cell's transcription machinery (as described above for cancer).

Homologs of the yNC2 protein can exhibit differences in sequence identity and these differences can be exploited in designing substances (e.g., drugs) that target eukaryotic pathogens without the interfering with the hosts' gene transcription machinery. For example, a drug can be identified, or designed, e.g., an antisense DNA sequence that hybridizes to a fungal yNC2 DNA sequence, and thus modify gene transcription in the fungus. The antisense oligonucleotide will specifically hybridize to fungal DNA, but will not hybridize with human DNA, thus, gene transcription in the human host is not compromised. Eukaryotic pathogens can include, e.g., fungi such as Candida or Pneumocystis; parasites such as Plasmodium and Schistosoma; pathogenic worms; and insects that affect animals or agricultural crops.

Introduction of a substance into the cell may be by any conventional means, such as the use of a carrier protein which will interact with the cell membrane; attachment to an antibody which reacts with a cell surface antigen; or encapsulation in a liposome. If the substance is proteinaceous in nature, e.g., a peptide, DNA encoding the substance can be introduced into the cell, and the substance can be genetically expressed in the cell. Alternatively, the DNA can be directly introduced into a cell, e.g., an epidermal cell, via a "gene gun", or other electroporation technique. Other methods of cell targeting known to those of skill in the art may also be used.

According to this invention, the substances can be formulated into pharmaceutical compositions containing a pharmaceutically acceptable carrier and/or other excipients using conventional materials and means. They can be administered using conventional routes such as parenteral, oral, inhalation and the like, using appropriate formulations. Other methods of passive or active transport of small molecules known to those of skill in the art can also be employed.

Suitable pharmaceutically acceptable carriers include, but are not limited to, water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxymethy-cellulose, polyvinyl pyrrolidone, etc. For parenteral application, particularly suitable are injectable, sterile solutions, preferably oily or aqueous solutions, as well as suspensions, emulsions, or implants, including suppositories.

It will be appreciated that the actual preferred effective amounts of substance in a specific case will vary according to the specific substance being utilized, the particular compositions formulated, the mode of application, the particular situs of application, and the organism being treated. If administered to an individual, dosages for a given recipient will be determined on the basis of individual characteristics, such as body size, weight, age and the type and severity of the condition being treated.

Also encompassed by the present invention are methods of diagnosing disease conditions in humans resulting from abnormalities in the production of, or in the yNC2 protein itself. These methods are based on the detection, and/or quantification, of e.g., yNC2 protein, DNA or RNA in the cell, or in a biological sample. A biological sample includes biological fluids such as blood, urine, feces, tissue samples or cells isolated from these sources.

Encompassed by the present invention is a method of detecting yNC2 DNA encoding a yeast negative regulator protein in a biological sample comprising rendering nucleic acid present in a test sample suitable for hybridization with complementary DNA or RNA; contacting the nucleic acid of the test sample with a DNA or RNA probe which is a nucleic acid sequence complementary to all, or a portion of, the the nucleic acid sequence encoding a yeast negative regulator protein under conditions appropriate for selective hybridization to take place, and detecting hybridization of test nucleic acid with probe wherein hybridization of the probe with test nucleic acid is indicative of the presence of a nucleic acid encoding a yeast negative regulator protein. The probe typically is detectably labeled. Such detectable labels are well-known to those of skill in the art.

Nucleic acid probes useful in the described method can include all, or a portion of, SEQ ID NOS:1 and 3. The DNA probe would be a nucleic acid probe having a nucleic acid sequence of sufficient length and complementarity to a yNC2 DNA sequence such that it is capable of selectively hybridizing with yNC2 DNA under stringent hybridization conditions. These conditions may be conditions of moderate or high stringency, as determined by one of skill in the art. Detection and quantification of yNC2 DNA can be determined using standard techniques of detection, such as fluorescence detection, if fluorescent-tagged probes are used.

A Western blot can be used to detect, or quantify, the amount of yNC2 protein present in a cell using antibodies specific for yNC2, such as described herein.

An immunoassay, using either polyclonal or monoclonal antibodies, can be used to determine the biological activity of yNC2 protein. For example, a biological sample can be obtained and reacted with an antibody under conditions suitable for binding of the antibody to yNC2 protein. If the sample contains yNC2 protein, the antibody will bind to the protein, forming an antibody/yNC2 protein complex. This antibody/yNC2 complex can be detected using, for example, a second antibody which is detectably-tagged and which would bind to this complex as is known to those of skill in the art. Polyclonal antibodies specific for yNC2 are described herein. Monoclonal antibodies can be produced using methods well known to those of skill in the art.

This invention further relates to methods of treating disease conditions resulting from insufficient, or increased, production of, yNC2 protein, or production of abnormal yNC2 protein. These methods include the use of substances that bind to, or interact with, the yNC2 protein, genes encoding the yNC2 protein, yNC2 messenger RNA, or the use of genetically altered yNC2 protein.

The present invention is illustrated by the following examples, which are not intended to be limited in any way.

EXAMPLES

Example 1

Genetic Screen for Suppressors of Temperature Sensitive SRB4 Mutant RNA Polymerase II Holoenzyme The temperature sensitive phenotype of srb4-Z 138 strain (Z628) was used to obtain 93 independent suppressing isolates capable of growth at the restrictive temperature of 36° C. Genetic analysis revealed that 78 suppressors were extragenic and 15 were intragenic. Among the extragenic suppressors, 16 were dominant and 62 were recessive. The recessive suppressors were divided into complementation groups by switching mating types, mating suppressors of opposite mating types to each other, and testing the diploid strains for suppression at the restrictive temperature as described in Hengartner, C. J., et al., *Genes Dev* 9, 897–910 (1995). Five complementation groups were established. The yeast NCB1 gene (named NCB1 (Negative Cofactor B) because of its physical and functional homology to human NC2α/DRAP1 was cloned by complementation of group 1 using a wild type genomic DNA library, (Thompson, C. M., Koleske, A. L, Chao, D. M. & Young, R. A. Cell 73, 1361–75 (1993) and the insert of clone RY7135 was sequenced.

The sequence of NCB1 (SEQ ID NO:1); open reading frame (ORF) YER159c on chromosome V, GenBank accession number U18917) is shown in FIG. 1b. The suppressing allele, ncb1-1 was isolated by gap-repair techniques (Rothstein, R. *Methods Enzymol* 194, 281–301 (1991) and sequenced. The suppressing mutation, a single base pair deletion at nt 340, is noted in boldfaced type. The deletion results in a frameshift causing a translational stop at nt 347–349, also noted in bold faced type.

The yeast and human NC2α/DRAP1 protein alignment is shown in FIG. 1c. Vertical lines indicate identity; colons, comparison value >0.5; and dots, comparison value >0.1 as defined by the program BESTFIT. Underlined regions indicate sequence, homologous to the α-helices in the histone fold structure of histone H2A. (Mermelstein, F., et al., *Dev* 10, 1033–48 (1996)).

FIG. 1d shows the sequence of NCB2 (SEQ ID NO:3; open reading frame (ORF) D9509.16 on chromosome IV, Genbank accession number U32274) with a predicted intron. The alignment of yeast and human NC2β/Dr1 protein is shown in FIG. 1e. Underlined regions indicate sequence homologous to the α-helices in the histone fold structure of histone H2B. (Hoffmann, A., et al., *Nature* 380, 356–359 (1996); Xie, X., et al., *Nature* 380, 316–22 (1996)).

NCB1 is essential for cell viability

To determine whether the NCB1 gene is essential for cell viability, the entire coding region was deleted on one of the two chromosomes of a diploid cell, using standard procedures (Rothstein, R. *Methods Enzymol* 194, 281–301 (1991) and the plasmid RY7136 which carries the deletion allele ncb1Δ1. These heterozygous diploid cells were sporulated, and tetrad analysis performed. Spores with the ncb1Δ1 allele did not produce colonies, indicating that yNCB1 is essential for cell viability.

Yeast NC2a/DRAP1 is not a subunit of the RNA polymerase II holoenzyme

The identification of ncb1-1 as a suppressor of an SRB mutation indicates a functional interaction between yeast NC2α (DRAP1) and the RNA polymerase II holoenzyme. Since it is possible that yeast NC2α is a subunit of the holoenzyme we used quantitative Western analysis to determine whether NC2α could be detected in purified holoenzyme. Known amounts of purified RNA polymerase II holoenzyme (Koleske, A. J., Chao, D. M. & Young, R. A. *Methods Enzymol* 273, 176–84 (1996) and recombinant yNC2α/DRAP1 and SRB5 proteins were probed with anti-yNC2α/DRAP1 and anti-SRB5 antibodies. SRB5 is a standard previously used to quantitate holoenzyme subunits. (Wilson, C. J., et al., *Cell* 84, 235–44 (1996); Koleske, A. J. & Young, R. A. *Nature* 368, 466–469 (1994)). No NC2α/DRAP1 was detected in purified RNA polymerase II holoenzyme.

Yeast Strains and Plasmids

Yeast strains and plasmids are listed in Tables I and II.

TABLE 1

Yeast Strains

| Strain | Alias | Genotype |
|---|---|---|
| Z579 | CTY233 | Mat a ura3–52 his3Δ200 leu2–3, 112 srbΔ2: :HIS3 [pCT 127 (SRB4 LEU2 CEN)] |
| Z628 | CTY271 | Mat a ura3–52 his3Δ200 leu2–3, 112 srb4Δ2: :HIS3 [pCT181 (srb4–138 LEU2 CEN)] |
| Z804 | EGY83–88 | Mat a ura3–52 his3Δ200 leu2–3, 112 srb4Δ2: :HIS3 ncb1-1 [pCT 181 (srb4–138 LEU2 CEN)] |
| Z805 | EGY1141 | Mat a ura3–52 his3–200 leu2–3, 112 srb4Δ2: :HIS3 ncb1-1 [pCT15 (SRB4 URA3 CEN)] |
| Z806 | EGY115 | mat α ura3–52 his3Δ200 leu2–3, 112 ncb1Δ1: :HIS3 (pEG107 [pEG68 (NCB1 URA3 CEN)] |
| Z807 | EGY116 | Mat Δ ura3–52 his3Δ200 leu2–3, 112 ncb1WI: :HIS3 (pEG109) [pEG195 (NCB15' FLAG tag LEU2 CEN)] |

TABLE II

Plasmids

| Plasmid | Alias | Description |
|---|---|---|
| RY7133 | pEG99 | NCB1 in pGEX-4T-3 (Pharmacia) |
| RY7134 | pEG169 | NCB2 (encoding amino acids 13–146) in pGEX-4T-3 |
| RY135 | pEG68 | NCB1 (1.3 kb) URA3 CEN |
| RY7136 | pEG107 | ncb1Δ1::HIS3 in pBluescript II SK(+) (Stragagene) |
| RY137 | pEG195 | NCB1 5' FLAG tag (IBI) in pUN105 |

Example 2

Yeast NC2 (DRAP1/Dr1) Binds to TBP and Is Purified as a Two Subunit Complex

Rabbit polyclonal antibodies against yNC2α/DRAP1 and yNC2β/Dr1 were obtained against purified recombinant proteins derived from E. coli containing the pGEX-4T-3 (Pharmacia) constructs RY7133 and RY7134, respectively. Both antibodies were used to detect yNC2α/DRAP1 and yNC2β/Dr1 in Western blots at a dilution of 1:250 or 1:500.

Yeast NC2 (DRAP1/Dr1) was purified as follows. TBP-affinity chromatography was performed as described in Reese, J. C., Apone, L., Walker, S. S., Griffin L. A. & Green, M. R. Nature 371, 523–527 (1994), and 80 ml of the 1M KOAc eluate was dialyzed against buffer T plus 0.003% NP40. The dialyzed sample was applied to a 1 ml HiTrap SP cartridge (Pharmacia) at a flow rate of 1 ml/min, the column was washed with 10 ml of buffer A (20 mM K-HEPES pH 7.61 mM EDTA 10% glycerol protease inhibitors)+100 mM KOAc, and bound proteins were eluted with a 10 ml gradient of Buffer A from 100 mM to 1000 mM KOAc at a flow rate of 0.25 ml/min. Peak NC2 fractions were pooled, frozen in liquid nitrogen and stored at −70° C. until use. One ml of the SP eluate was diluted with 2.7 ml Buffer B (20 mM TrisOAc pH 7.81 mM EDTA 10% glycerol) and applied to a DEAE 5PW 5/5 column (Toso Haas) at a flow rate of 0.5 ml/min. The column was washed with 5 ml of Buffer B+100 mM KOAc, and bound proteins were eluted with a 12 ml gradient of Buffer B from 100 to 1000 mM KOAc. SDS PAGE and silver staining were performed as described in Koleske, A. J. & Young, R. A. Nature 368, 466–469 (1994).

Example 3

Highly Purified Yeast NC2 (DRAP1/Dr1) Inhibits Transcription by RNA Polymerase II Holoenzyme in vitro A strain containing functional FLAG-tagged yNC2α/DRAP1 was constructed as follows. Plasmid RY7137 was constructed by amplifying the NCB1 gene (including regulatory sequences) with two sets of overlapping primers to add a FLAG epitope (IBI) to the N-terminus of yNC2α/DRAP1. The two PCR products were gel purified, combined, and the entire FLAG-tagged NCB1 gene was amplified with primers adding 5' Hind III and 3' BamHI cloning sites. The final PCR product was cloned into plasmid pUN105 (Elledge, S. J. & Davis, R. W. Gene 70, 303–312 (1988). RY7137 was transformed into a Z806, a yeast strain containing the ncb1Δ1 deletion, by plasmid-shuffle techniques (Boeke, J. D., Trueheart, J., Natsoulis, G. & Fink, G. R. Methods Enzymol 154, 164–175 (1987) to produce Z807. The FLAG-tagged NCB1 was fully functional and able to complement the ncb1Δ1 deletion.

This strain was grown in YPD to late log phase, harvested by centrifugation, and 500 g of cell pellet was resuspended in 500 ml of 150 mM KOAC 60 mM K-HEPES pH 7.6 3 mM EDTA and protease inhibitors. The mixture was poured slowly into a bath of liquid nitrogen, excess liquid nitrogen was decanted, and the frozen cells were blended for 4 min. in a Waring blender. The blended cells were stored at −70° C. until use. The frozen mixture was thawed at 55° C. and centrifuged at 12,000 r.p.m. for 30 min. in a GSA (Sorvall) rotor. One volume (600 ml) of Buffer A+100 mM KOAc and 300 g of damp-dry BioRex 70 (BioRad) resin were added to the supernatant. After stirring for 2 hours, the BioRex 70 was washed with 1 l of buffer A+0.1M KOAc on a Buchner funnel and the washed resin was packed into a 5 cm i.d. column and washed with 0.5 l of buffer A +0.1M KOAc at a flow rate of 10 ml/min. Bound proteins were eluted with buffer A+1M KOAc. Fractions containing protein (115 ml at 4.1 mg/ml) were pooled, frozen in liquid nitrogen and stored at −70° C. until use. 32 ml of BioRex 70 eluate was thawed and mixed with 160 ml of Buffer B+protease inhibitors. The diluted eluate was centrifuged at 12,000 r.p.m. for 30 min. in a GSA rotor. The supernatant was applied to a 2 ml FLAG antibody M2 affinity column (IBI), the column was washed with 100 ml of Buffer B+150 mM KOAc and 10 ml Buffer+50 mM KOAc, and bound proteins were eluted with Buffer B+50 mM KOAc+50 μM FLAG peptide. The eluate (8 ml) was filtered through a 0.2 μ filter and applied to a Mono Q PC 1.6/5 column (Pharmacia) at a flow rate of 100 ul/min the column was washed with 1 ml Buffer B +50 mM KOAc+1 mM/DTT, and bound proteins were eluted with a 2 ml gradient of Buffer B+1 mM DTT from 50 mM to 2000 mM KOAc. SDS-PAGE, silver staining and Western analysis was performed as described in Example 2.

In vitro transcription reactions were performed as described in Koleske, A. J., Chao, D. M. & Young, R. A. Methods Enzymol 273, 176–84 (1996) except that 3' O-MeGTP was added to 40 μM, T1 RNase was omitted, and ethanol precipitations were performed with 400 instead of 600. Reactions were performed with increasing amounts of purified yeast NC2 (DRAP1/Dr1). Assuming a molecular weight of 64 K for NC2 (DRAP1/Dr1), 0.5 pmol was required for 50% inhibition of an equimolar amount of RNA polymerase II holoenzyme (estimated molecular weight 2,000 K).

Example 4

Loss of NC2 (DRAP1/Dr1) Function Compensates for the Global Defect in Class II Gene Expression Caused by the SRB4 Mutant Holoenzyme The ncb1-1 mutation suppresses the growth defect of the srb4-138 mutant strain at the restrictive temperature. Growth of wild type (Z579), srb4-13 (Z628), srb4-138 ncb1-1 (Z804), and ncb1-1 (Z805) strains in YPD medium was evaluated at 30° C. and after shifting to the restrictive temperature of 35.5° C. The global decline in mRNA levels at the restrictive temperature in srb4-138 mutant strain is alleviated by the ncb1-1 mutation.

Aliquots of cells were removed from culture at 0, 2 and 4 hours and total RNA wild-type, srb4-138, srb4-138 ncb1-1 and ncb1-1 was prepared as described in Thompson, C. M. & Young, R. A. Proc Natl Acad Sci USA 92, 4587–90 (1995). Equivalent amounts of RNA (2 μg) were applied to a slot blot and the filter was probed with [$^{32}$P]poly(T) as described in Thompson, C. M. & Young, R. A. Proc Natl Acad Sci USA 92, 4587–90 (1995). The decrease in synthesis of individual class II messages at the restrictive temperature in the srb4-138 mutant strain is reversed by the ncb1-1 mutation.

Equivalent amounts of RNA from wild type, srb4-138, srb4-138 ncb1-1 and ncb1-1 were hybridized with an excess of $^{32}$P-labeled oligonucleotide complementary to the transcripts, treated with Si nuclease, and subjected to denaturing polyacrylamide gel electrophoresis as described in Thompson, C. M. & Young, R. A. *Proc Natl Acad Sci USA* 92, 4587–90 (1995).

Equivalents

Those skilled in the art will recognize, or be able to ascertain, using no more than routine experimentation, many equivalents to the specific embodiments of the invention described herein. Such equivalents are intended to be encompassed by the following claims:

What is claimed is:

1. An isolated nucleic acid sequence encoding a yeast global negative regulator protein complex which represses class II transcription mediated by the RNA polymerase II holoenzyme, wherein the encoded complex comprises two subunit proteins, an α-subunit protein and a β-subunit protein and wherein the encoded complex represses transcription by binding to Tata-binding protein.

2. The isolated nucleic acid sequence of claim 1 wherein the nucleic acid sequence encoding the α-subunit protein is selected from the group consisting of: SEQ ID NO:1; the complementary strand of SEQ ID NO:1; and RNA transcribed from SEQ ID NO:1.

3. The isolated nucleic acid sequence of claim 1 wherein the nucleic acid sequence encoding the β-subunit protein is selected from the group consisting of: SEQ ID NO:3; the complementary strand of SEQ ID NO: 3; and RNA transcribed from SEQ ID NO: 3.

4. The isolated nucleic acid sequence of claim 1 wherein the encoded α-subunit protein comprises SEQ ID NO: 2 and the encoded β-subunit protein comprises SEQ ID NOS: 4 and 5.

5. The isolated nucleic acid sequence encoding the α subunit protein of claim 1, wherein the nucleic acid comprises SEQ ID NO: 1.

6. The isolated nucleic acid sequence encoding the β subunit protein of claim 1, wherein the nucleic acid comprises SEQ ID NO: 3.

7. An isolated nucleic acid sequence encoding a yeast global negative regulator protein complex comprising SEQ ID NO: 1 and SEQ ID NO: 3.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 648 base pairs
( B ) TYPE: nucleic acid
( C ) STRANDEDNESS: double
( D ) TOPOLOGY: linear ( i i ) MOLECULE TYPE: protein ( i x ) FEATURE:
( A ) NAME/KEY: CDS
( B ) LOCATION: 109..534

( x i ) SEQUENCE DESCRIPTION: SEQ ID NO:1:

```
TTTTATTTTG GGGCATTAAA ACCAAAAACG GAAAAAAAAG CACGTCACGA AAATAAAAAT           60

TCAAAAAAAA AAATAAAACC AGTTACAGTA CTCATCACTA CATTCTTA ATG GCA GAT          117
                                                    Met Ala Asp
                                                     1

CAA GTA CCA GTT ACA ACA CAA CTA CCA CCA ATA AAA CCT GAA CAT GAG           165
Gln Val Pro Val Thr Thr Gln Leu Pro Pro Ile Lys Pro Glu His Glu
      5                  10                  15

GTA CCA CTT GAT GCT GGA GGG AGT CCA GTA GGT AAC ATG GGT ACC AAC           213
Val Pro Leu Asp Ala Gly Gly Ser Pro Val Gly Asn Met Gly Thr Asn
 20                  25                  30                  35

TCG AAT AAC AAC AAC GAG CTA GGT GAT GTA TTC GAC AGA ATA AAG ACA           261
Ser Asn Asn Asn Asn Glu Leu Gly Asp Val Phe Asp Arg Ile Lys Thr
                 40                  45                  50

CAC TTC CCT CCG GCC AAG GTA AAG AAA ATA ATG CAG ACA GAC GAG GAT           309
His Phe Pro Pro Ala Lys Val Lys Lys Ile Met Gln Thr Asp Glu Asp
             55                  60                  65

ATA GGA AAA GTT TCA CAA GCC ACG CCC GTA ATA GCG GGC AGG TCC CTA           357
Ile Gly Lys Val Ser Gln Ala Thr Pro Val Ile Ala Gly Arg Ser Leu
         70                  75                  80

GAG TTT TTT ATA GCG TTA TTG GTG AAA AAA AGC GGG GAG ATG GCA AGA           405
Glu Phe Phe Ile Ala Leu Leu Val Lys Lys Ser Gly Glu Met Ala Arg
     85                  90                  95

GGA CAA GGA ACC AAG AGA ATA ACC GCC GAA ATA CTA AAA AAA ACA ATT           453
Gly Gln Gly Thr Lys Arg Ile Thr Ala Glu Ile Leu Lys Lys Thr Ile
100                 105                 110                 115

TTA AAC GAC GAA AAA TTC GAT TTC TTA AGG GAA GGT CTA TGC GTA GAA           501
Leu Asn Asp Glu Lys Phe Asp Phe Leu Arg Glu Gly Leu Cys Val Glu
                120                 125                 130

GAA GGC CAA ACA CAA CCG GAG GAA GAG AGT GCC TGAGCAGAAC GGGGCGATGT         554
Glu Gly Gln Thr Gln Pro Glu Glu Glu Ser Ala
                135                 140

AACTTAGTGT AAAATGAATA CCACATCTAT ATATATCCAT ATACCAATGT ATTTATATCT         614

ATATATGTCT GCACATATAT ATTATACTCT ATTA                                     648
```

( 2 ) INFORMATION FOR SEQ ID NO:2:

( i ) SEQUENCE CHARACTERISTICS:
  ( A ) LENGTH: 142 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

```
Met Ala Asp Gln Val Pro Val Thr Thr Gln Leu Pro Pro Ile Lys Pro
 1               5                  10                  15

Glu His Glu Val Pro Leu Asp Ala Gly Gly Ser Pro Val Gly Asn Met
            20                  25                  30

Gly Thr Asn Ser Asn Asn Asn Asn Glu Leu Gly Asp Val Phe Asp Arg
        35                  40                  45

Ile Lys Thr His Phe Pro Pro Ala Lys Val Lys Lys Ile Met Gln Thr
    50                  55                  60

Asp Glu Asp Ile Gly Lys Val Ser Gln Ala Thr Pro Val Ile Ala Gly
65                  70                  75                  80

Arg Ser Leu Glu Phe Phe Ile Ala Leu Leu Val Lys Lys Ser Gly Glu
                85                  90                  95

Met Ala Arg Gly Gln Gly Thr Lys Arg Ile Thr Ala Glu Ile Leu Lys
            100                 105                 110

Lys Thr Ile Leu Asn Asp Glu Lys Phe Asp Phe Leu Arg Glu Gly Leu
        115                 120                 125

Cys Val Glu Glu Gly Gln Thr Gln Pro Glu Glu Glu Ser Ala
130                 135                 140
```

( 2 ) INFORMATION FOR SEQ ID NO:3:

( i ) SEQUENCE CHARACTERISTICS:
    ( A ) LENGTH: 756 base pairs
    ( B ) TYPE: nucleic acid
    ( C ) STRANDEDNESS: double
    ( D ) TOPOLOGY: linear ( i i ) MOLECULE TYPE: protein ( x i ) SEQUENCE DESCRIPTION: SEQ ID NO:3:

```
TCGCCCTCTG CTCGCCTTGT CGATTTCTAT CGTGCAGAGT TACCAGTATA AGGTGGGCAA    60
GAAATCATAA CGATATTTAC TAATACAGTT GTACCTATTA ATTAATTGAT GGCTGGAGAC   120
TCCGATAATG TGTCGCTTCC CAAGGGTATG TTAGTTATAT TGTTGTTGCA AAACTCAAGC   180
TTTGATGCGG GTACTGAGCG GTTATACTAA CTTAGAGAAA ACACTGAATG ATCTTAGCGA   240
CCGTACAAAA GATGATATCT GAAATACTGG ACCAGGATTT GATGTTTACC AAGGATGCAA   300
GAGAAATCAT CATCAACTCC GGCATAGAAT TCATAATGAT CCTGTCCTCG ATGGCTTCCG   360
AAATGGCGGA CAACGAGGCT AAGAAAACCA TAGCGCCCGA GCACGTGATC AAAGCGCTAG   420
AAGAGTTGGA GTATAATGAG TTTATACCAT TCTTAGAGGA AATATTATTG AATTTTAAGG   480
GTTCCCAGAA GGTGAAAGAA ACTAGGGATT CCAAGTTCAA GAAGTCAGGT CTCTCGGAAG   540
AAGAGCTGCT ACGACAACAA GAGGAGTTGT TTAGACAGTC AAGGTCCAGA TTACACCACA   600
ATAGTGTATC TGATCCGGTT AAGTCGGAGG ATTCTTCTTG AATAGAAGCT TCTAAACAAA   660
GTAATGCTAT ATACGAAAAT AAACCACATG GGAATATGTT AAGCGCATGC ATGTATGTAA   720
TAAAAACGAA GACAAGTCCA AAAAAAAAA AGAACG                              756
```

( 2 ) INFORMATION FOR SEQ ID NO:4:

( i ) SEQUENCE CHARACTERISTICS:

(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

| Met | Ala | Gly | Asp | Ser | Asp | Asn | Val | Ser | Leu | Pro | Lys | Ala |
|-----|-----|-----|-----|-----|-----|-----|-----|-----|-----|-----|-----|-----|
| 1   |     |     |     | 5   |     |     |     |     | 10  |     |     |     |

(2) INFORMATION FOR SEQ ID NO:5:

(i) SEQUENCE CHARACTERISTICS:
(A) LENGTH: 133 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

| Thr | Val | Gln | Lys | Met | Ile | Ser | Glu | Ile | Leu | Asp | Gln | Asp | Leu | Met | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Lys | Asp | Ala | Arg | Glu | Ile | Ile | Asn | Ser | Gly | Ile | Glu | Phe | Ile |
|-----|-----|-----|-----|-----|-----|-----|-----|-----|-----|-----|-----|-----|-----|-----|
|     |     |     | 20  |     |     |     | 25  |     |     |     |     | 30  |     |     |

| Met | Ile | Leu | Ser | Ser | Met | Ala | Ser | Glu | Met | Ala | Asp | Asn | Glu | Ala | Lys |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Lys | Thr | Ile | Ala | Pro | Glu | His | Val | Ile | Lys | Ala | Leu | Glu | Glu | Leu | Glu |
|-----|-----|-----|-----|-----|-----|-----|-----|-----|-----|-----|-----|-----|-----|-----|-----|
|     | 50  |     |     |     |     | 55  |     |     |     |     |     | 60  |     |     |     |

| Tyr | Asn | Glu | Phe | Ile | Pro | Phe | Leu | Glu | Glu | Ile | Leu | Leu | Asn | Phe | Lys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gly | Ser | Gln | Lys | Val | Lys | Glu | Thr | Arg | Asp | Ser | Lys | Phe | Lys | Lys | Ser |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Gly | Leu | Ser | Glu | Glu | Glu | Leu | Leu | Arg | Gln | Gln | Glu | Glu | Leu | Phe | Arg |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| Gln | Ser | Arg | Ser | Arg | Leu | His | His | Asn | Ser | Val | Ser | Asp | Pro | Val | Lys |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ser | Glu | Asp | Ser | Ser |
|-----|-----|-----|-----|-----|
|     |     | 130 |     |     |

(2) INFORMATION FOR SEQ ID NO:6:

(i) SEQUENCE CHARACTERISTICS:
(A) LENGTH: 100 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:6:

| Met | Pro | Ser | Lys | Lys | Lys | Lys | Tyr | Asn | Ala | Arg | Phe | Pro | Pro | Ala | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ile | Lys | Lys | Ile | Met | Gln | Thr | Asp | Glu | Glu | Ile | Gly | Lys | Val | Ala | Ala |
|-----|-----|-----|-----|-----|-----|-----|-----|-----|-----|-----|-----|-----|-----|-----|-----|
|     |     |     | 20  |     |     |     | 25  |     |     |     |     | 30  |     |     |     |

| Ala | Val | Pro | Val | Ile | Ile | Ser | Arg | Ala | Leu | Glu | Leu | Phe | Leu | Glu | Ser |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Leu | Leu | Lys | Lys | Ala | Cys | Gln | Val | Thr | Gln | Ser | Arg | Asn | Ala | Lys | Thr |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Met | Thr | Thr | Ser | His | Leu | Lys | Gln | Cys | Ile | Glu | Leu | Glu | Gln | Gln | Phe |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

```
Asp Phe Leu Lys Asp Leu Val Ala Ser Val Pro Asp Met Gln Gly Asp
                 85                  90                  95

Gly Glu Asp Asn
            100
```

( 2 ) INFORMATION FOR SEQ ID NO:7:

( i ) SEQUENCE CHARACTERISTICS:
         ( A ) LENGTH: 156 amino acids
         ( B ) TYPE: amino acid
         ( C ) STRANDEDNESS: single
         ( D ) TOPOLOGY: linear ( i i ) MOLECULE TYPE: protein ( x i ) SEQUENCE DESCRIPTION: SEQ ID NO:7:

```
Ser Gly Asn Asp Asp Asp Leu Thr Ile Pro Arg Ala Ala Ile Asn Lys
1               5                    10                  15

Met Ile Lys Glu Thr Leu Pro Asn Val Arg Val Ala Asn Asp Ala Arg
            20                  25                  30

Glu Leu Val Val Asn Cys Cys Thr Glu Phe Ile His Leu Ile Ser Ser
            35                  40                  45

Glu Ala Asn Glu Ile Cys Asn Lys Ser Glu Lys Lys Thr Ile Ser Pro
    50                  55                  60

Glu His Val Ile Gln Ala Leu Glu Ser Leu Gly Phe Gly Ser Tyr Ile
65                  70                  75                  80

Ser Glu Val Lys Glu Val Leu Gln Glu Cys Lys Thr Val Ala Leu Lys
                85                  90                  95

Arg Arg Lys Ala Ser Ser Arg Leu Glu Asn Leu Gly Ile Pro Glu Glu
            100                 105                 110

Glu Leu Leu Arg Gln Gln Gln Glu Leu Phe Ala Ile Lys Ala Arg Gln
        115                 120                 125

Gln Gln Ala Glu Leu Ala Gln Gln Glu Trp Leu Gln Met Gln Gln Ala
    130                 135                 140

Ala Gln Gln Ala Gln Leu Ala Ala Ala Ser Ala Ser
145                 150                 155
```